United States Patent [19]

O'Donnell, Jr. et al.

[11] Patent Number: 5,002,571
[45] Date of Patent: Mar. 26, 1991

[54] INTRAOCULAR LENS IMPLANT AND METHOD OF LOCATING AND ADHERING WITHIN THE POSTERIOR CHAMBER

[76] Inventors: Francis E. O'Donnell, Jr., 6035 Lindell Blvd., St. Louis, Mo. 63112; Robert M. Nalbandian, 901 S. Skinker, Apt. E., Clayton, Mo. 63105; Eberhard Mammen, 652 Woods La., Grosse Point Woods, Mich. 48236

[21] Appl. No.: 306,691

[22] Filed: Feb. 6, 1989

[51] Int. Cl.$^5$ .............................................. A61F 2/16
[52] U.S. Cl. ......................................................... 623/6
[58] Field of Search ........................................... 623/6

[56] References Cited

U.S. PATENT DOCUMENTS

| | | | |
|---|---|---|---|
| 3,986,214 | 11/1976 | Krasnov | 623/6 |
| 3,991,426 | 11/1976 | Flom et al. | 623/6 |
| 4,159,546 | 7/1979 | Shearing | 623/6 |
| 4,240,163 | 12/1980 | Galin | 623/6 |
| 4,244,060 | 1/1981 | Hoffer | 623/6 |
| 4,298,996 | 11/1981 | Barnet | 623/6 |
| 4,346,482 | 8/1982 | Tennant et al. | 623/6 |
| 4,534,069 | 8/1985 | Kelman | 623/6 |
| 4,543,673 | 10/1985 | Drake et al. | 623/6 |
| 4,661,108 | 4/1987 | Grendahl et al. | 623/6 |

FOREIGN PATENT DOCUMENTS 234365  4/1986  Fed. Rep. of Germany .......... 623/6

OTHER PUBLICATIONS

"Ophthamalic Surgery"—vol. 18, No. 2, Feb. 1987, p. 156.
"Current Eye Research"—vol. 6, No. 6, Jun. 1987—K. Greene, et al., pp. 835–838.
"American Journal of Ophthamology"—vol. 102, Aug. 1986, pp. 199 through 207.
"Ophthalmic Surgery", vol. 18, No. 4, Apr. 1987, Microsurgical Treatment of Lens Capsule Perforations—Part II,—pp. 276–282.
"American Journal of Ophthamology"—vol. 27, 1944—Corneal Healing—A. Brown, M.D., et al., pp. 1220–1124.
"Investigative Ophthamology"—vol. 14, No. 11, Nov. 1975, pp. 872–875.
ANN Ophthalmol 1986, Nov.—pp. 324–327, The Use of Autogenous Rabbit Fibrin Sealant, etc.,—I. Nasaduke, M.D., et al.
"American Journal of Ophthamology"—vol. 104, pp. 127–132 Aug. 1987, Transvitreal Cyanonacrylate Retinopexy in the Management of Complicated Retinal Detachment—B. W. McCuen, II, M.D., et al.
"Thrombosis Research", vol. 12, No. 5, pp. 907–910, Pergamon Press Ltd., 1978, (Gt. Britian)—A. Stemberger, et al.

Primary Examiner—Ronald Frinks

[57] ABSTRACT

An intraocular lens for implanting in the posterior chamber of a human eye after an extracapsular extraction, the intraocular lens having adhesive means applied to its backside thereof, said adhesive means being applied either an annulus, around the outer perimeter of backside of the lens, or entirely over the backside of the lens, when implanted against the posterior wall, and has a tendency to effect tissue growth between said posterior wall and the adhesive means for effectively retaining the implanted intraocular lens in place; the adhesive means comprising either a biological glue, formed either as fibrin, comprised of an annular patch, or as a collagen, formed as an annular patch, or as a fibrin containing as an additive ingredient collagen particles, or being impregnated with lyophilized fibronectin, or the adhesive means may comprise a biological glue in the form of mussel glue, for adherence against the backside of the lens, either around its circumferential perimeter, or over the entire backside of the lens, during IOL implanting, or the adhesive means may comprise a nonbiological glue, or said adhesive means may comprise a combination of either a biological and nonbiological glue for adherence of the IOL in place after implanting.

29 Claims, 3 Drawing Sheets

# INTRAOCULAR LENS IMPLANT AND METHOD OF LOCATING AND ADHERING WITHIN THE POSTERIOR CHAMBER

BACKGROUND OF THE INVENTION

This invention relates generally to intraocular lenses (IOLs) for implant in the human eye and more specifically to an IOL for implantation in the posterior chamber after an extracapsular cataract extraction (ECE) where the IOL will adhere to the wall of the posterior chamber, i.e. the posterior capsule, by means of an adhesive, either a biological adhesive, or a nonbiological adhesive, and wherein the IOL will prevent the central migration of lens epithelium or other biological contaminents to and within the space between the IOL and the posterior capsule, while simultaneously retaining the lens in its affixed position, and prevent it from migration.

In 1949, the first IOL implants were performed using the Ridley lens. The Ridley lens was held in place by scarring it to the lens capsule and iris. However, it did not remain stable within the eye, as implanted, and further induced corneal dystrophy, glaucoma, and hemorrhaging. It was therefore soon abandoned and replaced by anterior chamber IOLs. The first anterior chamber IOLs were held in place by seating rigid (Strampelli lens, 1953) or by flexible (Danheim lens, 1955) positioning loops in the angle of the anterior chamber. The Strampelli rigid support lens caused corneal dystrophy and had inadequate fixation means which led to epithelial cell loss. The concept, was therefore abandoned. The Danheim lens' fixation loops haptics were made from nylon and were therefore subject to biodegradation in the eye. But, it too was soon abandoned as a concept for this type of implantation.

The problems associated with seating the haptics in the angle of the anterior chamber was addressed by turning to the iris itself for support. The earliest such lens was Epstein's "collar stud" lens which resembled a shirt's stud. It had frequent problems with dislocation due to its extreme weight. Epstein then designed his "Maltese Cross" lens which had four bracing haptics, or loops. Two of the loops were seated behind the iris, while the other two were seated in front of the same.

In 1957, Binkhorst designed his iris clip lens. The original design had four positioning loops—two "L" shaped loops protruded from the back of the lens and were seated behind the iris when inserted, once the other two loops projected from the side of the lens, coplaner with the bottom of the lens, and were seated in front of the iris. Binkhorst further designed a two loop lens and a cloverleaf lens to overcome the problems of dislocation and corneal decompensation associated with the original four loop designs. A number of inventors modified the Brinkhorst lens. For example, Krasnov used sutures to keep the lens fixed, as identified in U.S. Pat. No. 3,986,214. Flom utilized posts which projected rearwardly from the back of the lens, and which penetrated the iris, as shown in U.S. Pat. No. 3,991,426. Furthermore, Barnet utilized magnetic attraction to position the lens by placing magnets at the end of the loops on either side of the iris, as shown in his U.S. Pat. No. 4,298,996. In 1973, Worst designed his medallion lens, which had loops at the approximately three and nine o'clock positions, and a rim around the optical portion and which was sutured to the peripheral structure of the iris.

Early on, lenses had been designed for locating within the posterior chamber. In the mid-1950's Barraquer deigned a lens having incomplete, S-shaped, polypropylene loops which were to be seated in the capsular bag after an ECE. In 1975, Shearing designed a similar lens which also utilized flexibly incomplete loops to position the lens, as shown in his U.S. Pat. No. 4,159,546. Furthermore, the Shearing lens, like the Brinkhorst lens, had many modifications to it, to improve its ability to remain in position, once installed and located. The modifications included the altering of its configuration, size, and number of loops, or through the replacing of the loops with sets of straight pliant hairs, as can be seen in the Hoffer U.S. Pat. No. 4,244,060.

Many of these lenses developed opacified posterior capsules after implantation, and were generally unstable to varying degrees within the eye, once installed, or were damaging to the iris during implantation.

Opacification of the posterior capsule is due to the central migration of lens epithelium which could not be completely removed when the natural lens was removed. The epithelial cells migrate to the space between the implanted IOL and the posterior capsule of the eye. If they proliferate and create new lens fibers then "epithelial pearls" are formed. Some of the cells may metamorphose into myofibroplasts, which gives rise to connective tissue and create what is known as "fibrosis of the posterior capsule." These pearls and/or fibrosis impede and may eventually completely obstruct vision, requiring YAG laser treatment, or discission to restore the clarity. This problem has previously been addressed by Hoffer in his '060 patent, as explained above. Hoffer incorporated, as an integral part of the IOL, an annular lip or ridge which was implaced at the outer periphery of the lens and protruded rearwardly therefrom to the posterior surface of the eye cavity. The ridge, however, was not continuous. It had one or two openings to allow for the insertion of an ophthalmic instrument to perform a discission, a procedure required by IOL opacification due to the presence of such opacification. Because the ridge was not continuous, since the lens does not sit tightly against the posterior capsule and because lens epithelium can migrate, as shown in lab studies, under the ridge, the Hoffer lens is still subject to the formation of pearls and fibrosis after any prolonged usage.

Many posterior chamber lenses use polypropylene, or polymethyl methacrylate, a flexible and memory retaining material, for their positioning hairs or loops ("haptics") that are structured onto the lens, for fixation purposes. After a period of time, though, the memory retaining ability of the haptics may be lost, at which time, the IOLs have a tendency to decenter. Further, implanting lenses with protruding fixation means can damage the Uveal tissue if the haptics are not inserted into the capsular bag. Damage can occur if the haptics are passed through the pupil to be seated in the saddle or cul-de-sac of the posterior chamber. (The ciliary sulcus.) Kelman, in his U.S. Pat. No. 4,534,069, addressed this problem by securing the positioning means in a contracted position around the IOL using a soluble coating. When the lens is inserted through the pupil, the hairs, or loops, then do not damage the iris. Once inside the posterior chamber, the coating dissolves and the positioning means extend to seat themselves in the posterior chamber cul-de-sac. This method, however, requires the surgeon to hold the lens in place while the positioning means extend. Further, this lens is still subject to instability, the gradual formation of the detrimental pearls.

A lens which uses an adhesive such as the body's coagulation system, then such an adhesive could solve the above-mentioned problems. Because the IOL optic would be glued to the posterior capsule, it would remain in place without the fear of haptics eventually failing. And, because the haptics are not required, the potential for Uveal contact would be minimal. Furthermore, the adhesive could form a barrier to the central migration of lens epithelium, and thus prevent post-implantation opacification of the posterior capsule. Presently, there are no such adhesive-lenses available.

The use of a biological glue has, however, been used in other areas of medicine. For example, in 1940, the use of a fibrin coagulum was introduced as a substitute for nerve sutures and was later introduced for use in conjunction with skin grafting. In 1944, the use of aqueous fibrin was examined to replace sutures in the eye wounds. However, human aqueous fibrin was found not to be sufficiently adhesive due to the small amounts of fibrinogen present in the aqueous.

The search for a biological glue for use in the eye slowed until the 1970's. In 1975, a mixture of autogonous platelets, human fibrinogen, and bovine thrombine (pft) were introduced for use in autotransplanted lamellar keratoplasties in rabbits. In this study, the cornea was removed, and the p-f-t mixture was applied in sequence to the lamellar bed. The cornea was then replaced without the use of sutures. A week after surgery, the adhesive began to disappear and fibroplaste growth was evident along the boundary of the adhesive. After two weeks, the adhesive had been absorbed and was no longer visible. The p-f-t adhesive was found to be nontoxic, soft, rubbery and pliable, and to be absorbed by the rabbit. This method, however, also allowed continued epithilial growth. This growth cannot be tolerated when implanting IOLs, for reasons as previously explained, since it will and does lead to opacification of the posterior capsule.

In 1986, an autogenous fibrin sealant consisting of bovine thrombin, plasma, and $CaCl_2$ was injected into a retinal hole and under the retina to seal retinal detachments in rabbits. This exercise was, however, unsuccessful, in that the results of sealant treated and control retinas were very similar.

In 1987, human fibrinogen concentrate was successfully used to close lens capsule wounds and through-and-through lens perforations. Equal amounts of fibrinogen concentrate and thrombin-$CaCl_2$ solution were successively applied. The fibrinogen was forced through the perforation path and the thrombin-$CaCl_2$ was then injected into the posterior and anterior chambers.

Also, as disclosed in the East German patent specification, DD234365A1, the concept of implanting a lens, in conjunction with an adhesive, was shown in 1985. In that particular instance, the artificial eye lens having small holes located spacedly through its periphery was applied by means of a nontoxic nonabsorbable tissue adhesive, by applying the adhesive through the holes, to implant the lens to the posterior capsule of the eye. While this particular concept was to provide a means for adhesively connecting an artificial lens to the posterior capsule, it is undetected from the published specification as to whether the adhesive formed a perfect seal, entirely around the periphery of the implanted lens, and as to whether or not posterior capsule opacification would thereby be alleviated, after its implantation. Since only four such holes were shown in the patent's specification, and the adhesive was applied only at four discrete locations, it is likely that complete sealing could not, or would not, have taken place.

In addition to the foregoing, various biological glues have been developed by a company named Bio-Polymers, Inc., and which adhesive or coating formulation comprises a bioadhesive polyphenolic protein component, with a proteinaceous substance, including cross linking agents, to promote the desired properties of the formulation during usage. The formulations are identified for usage as adhesives, amongst other uses, for orthopedic repair to bones, etc., as an ophthalmic adhesive for aiding the healing of perforations, lacerations or incisions, as an ophthalmic adhesive for attaching the retina and for repair of lenses, and the like. Other biological adhesives of this Company are for use in promoting cell adhesion in tissue culture systems, may be used in cell-coated prostheses, or for use for implantable materials.

Furthermore, there are other settable adhesives that have been available in the art, generally of the non-biological type, and which also have even included in their usage medical applications, such as for application to wounds, cuts, or the like, to stimulate sealing or closure of such abrasions.

Summary of the Invention

A principal object of this current invention is to provide an intraocular lens implant wherein a nontoxic, nonabsorbable adhesive, that preferably functions in cooperation with the patient's own coagulation system is used as an effective sealant, to form a continuous, annular or disc like barrier against the migration of lens epithelial cells along the posterior capsule of the patient's eye. Essentially, the concept of this invention is to provide means for implanting an IOL within the posterior capsule, against the posterior chamber, and through the usage of the application of a glue, either of a biological type, such as one formed what is identified in the medical profession as fibrin, which is a biological solid sheet of adhering material, or through the use of a mussel-glue, either formed as an annulus, or a continuous sheet, or in the alternative, through the application of a nonabsorbable, nontoxic, transparent, an aqueous type of non-biological glue, such as those available in the art, for application to the entire backside, or at least around its circumferential perimeter, of the IOL, during its implanting. This achieves two very significant purposes. One, through the use of either of these types of adhesives, it provides for a solid adherence of the implanted lens against the posterior wall, provides for securement of the lens permanently in place, and because these adhesives, at least in the first instance, are biologically derived, have a tendency to react with the natural healing elements of the capsule surface, to form adherence between the posterior wall and the backside of the implantable lens, to achieve its locating in position. When performing this function, the ophthamologist may utilize a lens which may or may not include any positioning haptics, or even include haptics that may be absorbable, and eventually dissolvable, to aid in the locating of the lens in place, particularly while the adhesive is curing, or setting, to provide a very fixed location for the lens once implanted. In the second instance, the desireable feature and principle object of this invention is to prevent, through the usage of either a perimeter or backside coating of the entire lens, through the use of one of the glues identified herein, to prevent that epithelial migration, of pearls, as they are called, from migrating into that position between the backside of the IOL, and the posterior wall of the capsule, and which, in prior applications, has tended to cause opaqueness, aberrations in lens focusing, which is generally detrimental to the proper functioning of any lens implant.

Another object of this invention is to provide an IOL optic design which may be glued into position against the posterior capsule of the eye through the usage of non-toxic, non-absorbtive, adhesives. Such IOL features as bifocal ability are particularly well-suited for such optic modification because of the critical need for centration within the eye.

Still another object of this invention is to provide an IOL that may be positioned within the eye without the use of the usual haptics as so commonly used with prior art artificial lenses, or in the alternatnive, with the use of absorbable haptics allowing for stable centration until curing occurs.

Yet another objective of this invention is to provide an IOL that may be implanted in the posterior chamber of the eye, without incurring damage to the uveal tissue by contact.

These and other objects will become more apparent to those skilled in the art upon reviewing the summary of this invention, in addition to undertaking a study of its preferred embodiment, in view of the drawings.

In accordance with these objectives, there is provided an intraocular lens for implant within the posterior chamber of a human eye, after an extracapsular extraction has been performed, with the implantation of the lens being performed through the application of "glue" as applied to its peripheral back edge thereof. The glue is preferably one which is biologically formed, although any of the nontoxic, nonbiological glues may be effective. In the case of the former, it will interact with the patient's naturally occurring biological coagulation system to permanently secure and seal the IOL in place against the posterior wall, without the use of any permanent positioning hairs (haptics) or clips, or sutures, but at the same time, provide a means which will create a barrier to the central migration of any lens epithelium along the posterior capsule.

The glue is preferably applied only to the outer periphery of the backside of the IOL optic, and therefore has no detrimental effects upon the imaging and focusing characteristics of the constructed artificial lens, and through the location of the glue at this position, forms a continuous uninterrupted annulus or ridge thereat. This will prevent any possible aberrations in focusing of the lens, as aforesaid, which may otherwise occur if the glue is applied to the whole backside of the IOL. If the glue is transparent, however, it could be applied to the whole back surface of the lens, and be effective for our purposes herein. The glue will also act as a barrier to the central migration of lens epithelium, which has been a difficiency with earlier embodiments, as previously explained herein.

The glue may be any nontoxic, nonabsorable adhesive such as a fibrin based or a collagen based hemostat. The glue is preferably, though, a fibrin based hemostat, because, the collagen lacks the adhesive properties of the fibrin. The fibrin glue's adhesive properties may be enhanced by impregnating the glue with collagen particles and/or lyophilized fibronectin. After a short period of time, the fibrous connective tissue that inherently develops will grow around the annulus and permanently anchor, while simultaneously seal, the IOL to the posterior capsule of the eye. On the other hand, this is true, and will naturally occur, for both the fibrin and collagen based hemostats.

The glue may alternatively be a mussel glue. Because mussel glue does not adhere as quickly as fibrin or collagen based hemostats, the IOL will probably include positioning haptics, to hold the lens in position during adhesive or glue setting. However, these haptics may be either absorbable or of the dissolveable type, within the human eye, with the absorbing or dissolving to occur after the glue has set, since by that time, the haptics will no longer be required to provide for accurate positioning of the lens in place. Because mussel glue may be transparent, it might be applied to the whole backside of the lens, as opposed to merely applying it as a peripheral annulus, as previously explained. Furthermore, and for the same reason, it is likely that one of the nonbiological type of glues, as to be hereinafter defined, could also be utilized for the same purpose, during lens application. Nevertheless, when the variety of adhesive or glues are applied herein, and utilized for the purposes of this invention, once they are set, and hold the lens permanently against the posterior wall of the capsule, the lens is effectively fixed into position, the natural biological growth patterns of the surface of the posterior wall or the tendency to achieve biological coagulation to permanently secure and seal the IOL in place, as previously explained. For this reason, the concept of this invention is highly effective in holding those type of IOLs into position, once in place, such as those which may be formed as bifocals, and which require extreme precision in their location and implacement, with the capsule, during ophthamalic surgery.

DESCRIPTION OF THE PREFERRED EMBODIMENT

Figure 1:
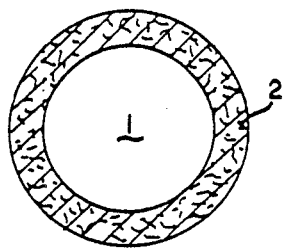
FIG. 1 is a back view of the IOL showing the fibrin annulus.
Figure 2:
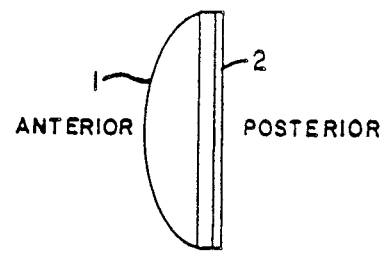
FIG. 2 is a lateral or side view of the IOL.
Figure 4:
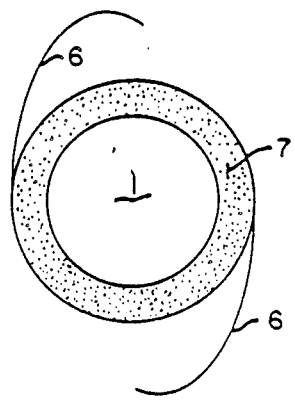
FIG. 4 is a back view of an IOL, with haptics, and a circumferential layer of glue applied thereto in preparation for implanting.

In referring to the drawings, and in particular FIGS. 1 through 6, the subject matter of this invention is disclosed, and includes the implacement of an IOL 1 for location within the posterior chamber of the eye, as designated at 4, within FIG. 4. An adhesive "glue" 2, is placed upon the backside of the lens, and while it is possible that the glue could be applied to the entire backside of the IOL, in the preferred embodiment, it is desireable that it be located at the peripheral rear of the disclosed lens. However, as previously summarized, to avoid distortions in the lens focusing, when applied within the human eye, the glue is preferably applied as an annulus around the outer perimeter of the IOL, as explained. This annulus could be cut from the sheet of fibrin material, which due to its inherent tacky consistency, is easily permanently adhered to the back side of the implantable lens. On an IOL of approximately 7 mm in diameter, the annulus formed of the adhesive is approximately 1-2 mm wide, leaving a 5-6 mm diameter circle within the center of the IOL optic that is devoid of any adhesive, or any other applied material whatsoever. The glue is applied such that the annulus is approximately 0.05 mm to 0.10 mm in depth.

As shown within these FIGS. 1 through 6, the type of "glue" that may be utilized for adhering the lens in place, may be, as previously summarized, either a nonbiological type of adhesive, but preferably, will be of the biological type. For example, various types of biological glues are available, such as the so-called mussel glue, which is formed and identified as a mussel adhesive protein (MAP), and is manufactured by the marine mollusk mytilus edulis to provide an attachment to substrates in a commonly turbulent environment. For example, it is readily understood that various mussels, in the sea, have inherent means for securement of themselves to a particular surface, and can remain in place, notwithstanding the heavy wave form and tidal environments that would under normal circumstances easily shift any unanchored item. But, the adhesive that the marine mollusk develops has been found to be very effective, in providing adherence, and it has been processed for usage for, at least testing purposes, in ophthamalic and other experimental epikeratoplasty.

In addition, a biological adhesive in the category of fibrin, as previously explained, and which is available from a West German company, named Beringwerke, located in Marburg, West Germany, has likewise been designed for usage for the current purposes, for holding an IOL in place, once implanted. As previously explained, this fibrin is available from the identified Company, and is generally formed from biological sources, usually being bovine derived, but, more currently, fibrin is now derived as a procoagulant from human origin, and is then pasteurized to maintain a bacteria free condition in preparation for its usage in the medical field, as herein defined.

Figure 7:
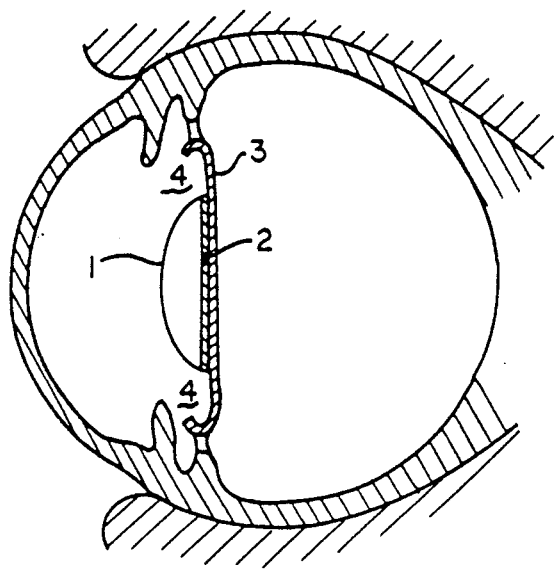
FIG. 7 is a cross-sectional view of the eye showing the IOL of FIG. 1 in place located against its posterior capsule.

Preferably, the adhesive is one which works in conjunction with the patient's own coagulation system, as previously explained, in order to form a natural bond between the lens 1 and the posterior wall 3, of the eye, to which the lens is adhered. See also FIG. 7. This "glue" preferably consists of a fibrin based hemostat, as summarized, such as the fibrin glue manufactured by said Behringwerke A.G., and which glue has strong adhesive properties, inherent in it, and which may be molded to fit any desired contour or shape, to which it is applied, and in its functioning, has been found not to be irritating to the patient, and which is ultimately biologically resorbed by the patient, and more particularly the posterior wall, as aforesaid. As can be noted in FIG. 3, the fibrin, when it is used as the type of adhesive, will preferably include a form of covering material, as at 5, and which may be peelable, for removal, just prior to the application of the IOL in place. Preferably, such covering materials 5 are readily available in the art, such as glassine paper, or other polymers, that are used for temporary coverings for pressure sensitive adhesives, as currently available in the trade. The adhesive properties of the fibrin matrix may be strengthened by impregnating it with collagen particles and/or lyophilized fibronectin, both of which induce the fibrin based matrix to be more interactive with the patient's procoagulents, inherent in such posterior wall.

Figure 8:
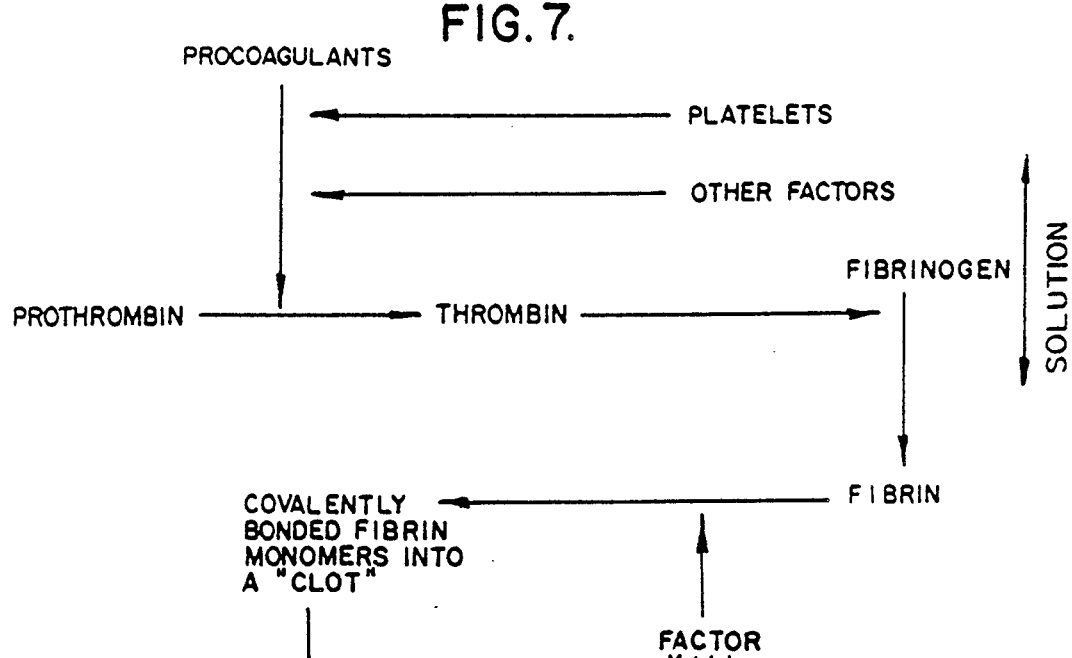
FIG. 8 is a chart disclosing the mechanism for formation of the fibrous tissue as it anchors the IOL to the posterior capsule.

When a fibrin based hemostat is used, the fibrin annulus immediately becomes adherent to the lacerated viscera, due to the fibrin's inherent tackiness, and thereby effectively arrests bleeding from the large cross-sectional area. The fibrin based hemostat adheres to the IOL, and more particularly to the posterior wall, via the process as depicted and shown in the graphic representation disclosed in FIG. 5. Thrombin is present in the body in an inactive form as a prothrombin. Prothrombin is converted to thrombin in the presence of calcium and thromboblastin, which is an intracelluar substance that is released when a physical cell is ruptured. In the case of a lens implant, the thromboblastin is released when the cornea is incised. The liberated thromboblastin then converts prothrombin to thrombin which in turn converts fibrinogen to fibrin. The fibrin then creates the connective tissue which adheres the lens to the posterior wall structure of the eye. See definition in FIG. 8.

Figure 5:
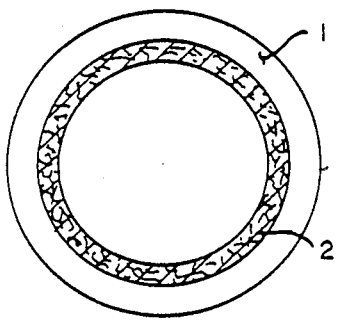
FIG. 5 is a back view of a modified IOL showing the recessed seating of the fibrin annulus proximate a peripheral edge.

The fibrin is considered as a practical manner in which to adapt the coagulation system of the eye in combination with the implanted lens, to provide for fixation of the lens in place. The fibrin annulus is insoluble, adhesive to the extent of being sticky to touch, and thus is capable of overcoming any prohibitive features of the liquids in the eye to resist adhesion, to allow the lens to be immediately implanted in place. After implanting, the action of the fibrin with abraded tissues of the surface of the posterior wall of the capsule undergoes a complicated biochemical change, wherein the soluble fibrinogen is converted to thrombin, and then into a insoluble, polymerized state. The fibrinogen dimmers are altered to fibrin monomers by thrombin which are then converted in a polymerized system composed of fibrin monomers acted upon by Factor VIII to form co-valent bonds. The insoluble fibrin thus is composed of strands of interlinked components which are spring loaded to undergo lysis. On the strands of insoluble, co-valently linked fibrin, there are posited molecules of plasminogen. For this enzyme system to become activated and for lysis of the fibrin to proceed, the presents of plasminogen activator is required to convert plasminogen (profibrinolysin) to plasmin (fibrinolysin). But there is no plasminogen activator in the aqueous humor of the anterior or posterior chamber of the eye. Hence, fibrin will remain stable in the posterior chamber with the lens capsule post-ece. Such fibrin preparations have been used for visceral hemostasis successfuly and it is now marketed for such purposes. The fibrin as used is an insoluble, co-valently linked adhesive fibrin which can be fashioned into rings or annuli and affixed to the posterior aspect of the IOL. And, as shown in FIG. 5 of the drawings, the annulus may be located either at the outer circumferential edge, or as disclosed therein, slightly interiorly thereof, and in addition, in order to provide for proper mounting, within the posterior capsule, the fibrin may even be recessed, slightly, within the IOL, to provide for flush mounting. Thus, seating of the fibrin annulus can be achieved, as noted.

The "glue" may alternatively be comprised of a collagen based topical hemostat such as Avitene, a microfibrillar collagen hemostat (MCH), such as produced by the Surgical Products Division of Alcon Laboratories, Inc., of Ft. Worth, Texas, and is available either in powdered form or as a non-woven-web form, or under the name Hemopad, a collagen based hemostat very similar to Avitene. Unlike the fibrin based glue, the collagen based adhesive has no adhesvie properties.

The collagen anchors the IOL optic to the posterior capsule of the eye using a different form of mechanism. The collagen operates as a sheet of paper which can be wrapped around the bleeding site. When in contact with a bleeding site, the MCH, which adheres very well to surfaces wetted with blood, attracts platelets which adheres to the fibrils and undergoes the release phenomenon to trigger aggregation of platelets and to thrombin in the interstices of the fibrous mass.

When a fibrin or collagen based hemostat is used, the hemostat works in conjunction with the patient's collagulation system to form a natural glue or adhering means. The fibrous connective tissue eventually grows along the annulus, permanently anchoring the IOL to the posterior capsule, and forming a barrier to the central migration of lens epithelium, as previously explained. Once the fibrosis is present, the IOL is permanently in place. A biological covalent bonding occurs between the fibrin annulus and the posterior capsule to adhere the lens in place. And, it has been found that even after prolonged installation, little or no dissolving of the fibrin takes place that would cause a dislodging or decentration of the implanted IOL. There is, however, a seven to ten day period of time after initial implantation, wherein the IOL can be easily removed by the use of tissue plasminogen activator (tPA). Since plasminogen was deposited in the fibrin interstices at the time the fibrin was formed from fibrinogen, tPA, a fibrinolysin, may be used to sever any connective tissue which has formed to remove or reposition the lens in place. It should be stated that the natural tackiness of the "glue" when applied as an annulus to the backside or rear wall of the IOL provides for its permanent adherence therewith, and to hold the lens in place, once located, so that the tissue growth that then naturally occurs between the fibrin adhesive and the tissue properties of the posterior capsule, have a tendency to provide tissue growth at the periphery, and along the edge of the implanted IOL, to maintain the same in place. And, the pressure of the capsule of the eye against the implanted lens further has a tendency to hold these various components together, while tissue growth occurs over a period of time.

In any event, the implanting of a lens within the eye through the usage of the materials as herein defined provides a significantly effective way to hold the lens in place, without the need for usage of various appendages such as permanent haptics, or the like, and in addition, allows for the lens to naturally be held in position by means of connective tissue growth, through the addition of the fibrin and/or collagen adhesive into the position as herein described. Such material has a fibrous like woven texture and is formed in a mat configuration, cut to size, and adhered to the back periphery of the lens for location within the eye, to allow tissue growth to permeate through and around the adhesive material to sustain the lens in place.

It is also likely that various types of nonbiological form of glues may be utilized for the same purpose of this invention. Particularly, such nonbiological adhesives may be used in the similar manner as that of the mussel glues, of the biological type, as previously explained. Such glues, and whether it be of the biological or nonbiological type, obviously must be nonabsorbing, so that once applied in place, with the IOL, it will not be dissolved, and allow the IOL to shift, or be removed from its mounting. In addition, such glues must be nontoxic, for obvious reasons. Furthermore, and while it is the general concensus of this invention that the adhesive, and whether it be of the biological or nonbiological type, or even fibrin, may preferably be applied at the circumferential edge or around the perimeter of the lens, to achieve a mounting of the IOL in place, and therein function as an effective mount for the lens, and likewise, prevent pearl migration to the center of the lens, a hazzard which has been previously explained, it is just is likely that such adhesives may likewise be applied over the entire back surface of the lens, just prior to implanting. Thus, and for obvious reasons, such glues, and whether they be of the mussel type, comprising a biological form of glue, or of a nonbiological type of adhesive, will have to be transparent, particularly after setting, so as not to detract from the focusing power and visual attributes desired from the lens, once in place. Furthermore, such glue must be of an aqueous consistancy, so that it can be easily applied to the back wall of the lens, whether it be over the entire surface of the lens, or at its perimeter, just before the lens is being implanted.

The mussel glue, where it is used, desirably enhances cell growth and tissue adherence to the lens, but, for obvious reasons, it does not set as quickly as does the tacky fibrin, when it is applied in conjunction with the lens. Hence, as can be seen in FIG. 4, where one of the biological or nonbiological glues may be used, for adhering the lens in place, it may be necessary to provide some temporary haptics, as at 6, to provisionally hold the lens in place, once implanted, and to retain it in such position, until such time as the glue, as disclosed at 7, may have set or dried. Obviously, since the haptics will not be a permanent requirement, it is likely that any type of absorable haptics, or those that may be capable of eventually dissolving, may be used, and be biologically removed by the natural fluids of the eye, after the lens has been held in place for some time, by them, once implanted.

In addition to the foregoing, various nonbiological glues may likewise be used, and must have the same attributes as the biological glues, as previously explained. Such glues must also be nontoxic, nonabsorbable, transparent when set, and of an aqueous consistancy, to facilitate their application. Glues in the category of the various polymer glues, or other adhesives, such as one containing an isocyanoacrylate type glue, as used in the medical field, may be applied.

Figure 6:
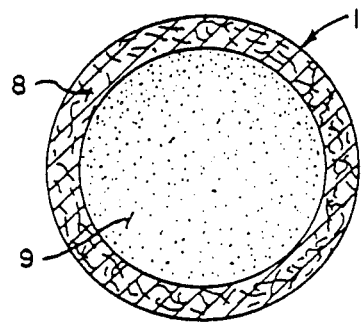
FIG. 6 is a back view of a modified IOL showing a fibrin annulus, at the circumferential edge of the lens, and with a biological, or nonbiological glue applied interiorly thereof, and to the back of the said lens.

As can be seen in FIG. 6, a combination of biological and nonbiological adhesives may likewise be utilized to provide for lens implant. As noted, the lens 1 may use, for example, an outer annulus of fibrin, as at 8, to provde for ready adherence and tacking of the lens to the capsule, and in addition, to provide for more permanent mounting, the usage of one of the biological such as mussel glue, or nonbiological glues, may be applied interiorly thereof, as at 9, to furnish a very permanent mounting of the IOL in place. This is just an example as to how the combined types of glues may be utilized for adherence of the IOL in place, with the fibrin providing for ready tacking of the IOL into location, the central glue furnishing long term adhesion, and likewise, with the combination of epitheleal growth, affording an effective fixation of the IOL in place, once implanted.

Figure 3:
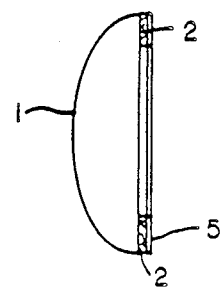
FIG. 3 is a lateral cross-sectional view of the IOL showing the ridge of the glue or fibrin annulus applied upon the backside of the implant lens, and a glassine or polymer pealable cover when the fibrin is employed, and located essentially around its periphery.
Figure 9:
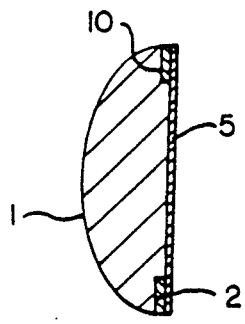
FIG. 9 is a lateral cross-sectional view of the IOL showing how the fibrin annulus may be applied recessed upon the backside of the implant lens, and a glassine or polymer peelable cover applied over the fibrin, and perhaps the backside of the lens, to provide sanitation for the fabricated product.
Figure 10:
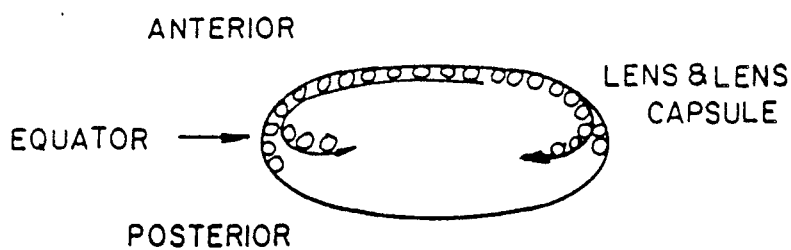
FIG. 10 is a schematic view of a cross-section of a lens capsule showing how epithelial growth can occur in the natural lens to cause cataract or related problems.

FIG. 9, in a similar arrangement to that as disclosed previously in FIG. 3, shows how the lens 1 may have its fibrin annulus 2 recessed around its perimeter, in a position where the lens may have been formed or molded with an externally arranged counterbore, as at 10, to accommodate the locating of the fibrin annulus therein. Then, the pliable or glassine cover 5 may be added to preserve cleanliness, and a nonbacteria condition, until the time the IOL is implanted.

The arrangement for the lens as shown in FIGS. 3, and 9, on the other hand, require some analysis. Where the fibrin annulus is located directly upon the backside of the lens, as shown and explained in FIG. 3, this will provide an interior spacing, behind the lens, and between the posterior wall, as can be understood. Hence, this provides a spacing that allows for the circulation of eye fluids therein, after the IOL has been implanted, and which may provide a desirable feature that enhances the functioning of the implanted lens. On the other hand, as explained in FIG. 9, where the fibrin annulus is recessed within a counterbore provided around the perimeter of the lens, once the IOL is implanted, the back wall of the lens will be flush with the posterior wall of the capsule, and thereby provide little or no spacing against the said wall within which occular fluids may circulate. This may also be a desirable feature, it probably will prevent any spacing in which epithelial growth can occur, and therefore, reduce any aberrations in the vision of the eye in which the IOL is implanted.

As previously explained, the fibrin type of adhering means may be used totally independently with the IOL for adhering it directly to the posterior wall of the capsule, or, in the alternative, the type of biological or nonbiological form of glue, such as the previously identified muscle glue, may be used, for adhesion purposes. Either way, the two embodiments may be independently employed for mounting of the IOL in place. Or, in the third alternative, a combination of the two may be used.

Figure 11:
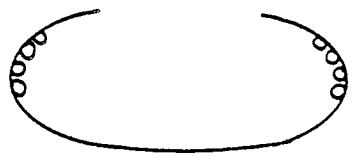
FIG. 11 is a view of the natural lens having been dissected at its surface to provide interior exposure for the surgeon.
Figure 12:
FIG. 12 discloses the surface dissected lens with the IOL and its attached fibrin connector being located towards the posterior wall.
Figure 13:
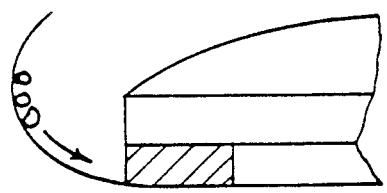
FIG. 13 shows a partial schematic of the IOL with its fibrin annulus being applied against the posterior wall of the capsule during implanting, disclosing how epithelial growth will be retarded from entering towards the interior of the backside of the implanted IOL.
Figure 14:
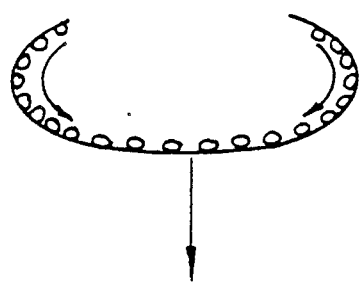
FIG. 14 discloses how epithelial growth occurs in a dissected lens without the implanting of an IOL.
Figure 15:
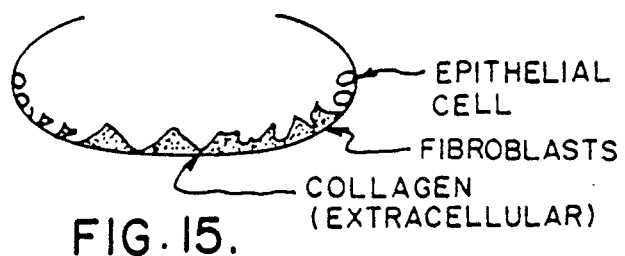
FIG. 15 is a schematic sectional view of an eye capsule disclosing how epithelial growth and collagen formed opacification occurs in a natural lens to effect loss of vision.

FIGS. 10 through 15 provide a brief schematic, in series, furnishing an understanding of the biological factors that occur in the implanting of a lens in place, in this particular instance, through the usage of the fibrin type of adhesive. For example, in FIG. 10, this provides a schematic cross-section of the natural lens and capsule, disclosing how epithelial growth can occur, generally at the equator location, as during the forming of a cataract. FIG. 11 shows the same capsule after the ophthamologist has incised a cut and removal of the anterior portion of the capsule, for attaining access to its natural lens, for removal. This shows the lens capsule after ECE, with the persisting location of the lens epithelial cells that generally remain at the capsule equator. Following this, as disclosed in FIG. 12, the IOL with its attached fibrin annulus are both positioned as a single unit within the capsule, and directed towards its posterior wall for application. As can be seen in FIG. 13, the IOL, with its fibrin annulus, and which has a very tacky form of surface texture, is applied against the posterior wall of the capsule, as implanted. The fibrin annulus, in its location, for holding the IOL in place, is converted into an adherent scar anteriorly and posteriorly within the capsule, and it has been found that clots form and convert into a fibrous type of scar, at a peripherial location, thereby preventing any central migration of epithelial cells towards the backside of the lens. The posterior and centrally arranged IOL, within the capsule, remains relatively clear at its central location, because the scar tissue forms at the location of the fibrin annulus, at a peripherial location, generally prevents the migration of epithelial cells inwardly thereof, so as to provide clear viewing, through the IOL, thereby preventing any opaqueness of viewing. As can be seen in FIG. 14, without the adherence of a lens into the capsule, within four to eight weeks after ECE, lens epithelial cells migrate posteriorly over the central surface of the lens capsule, it effects metamorphis into fibroblast, lays down and extracellular layer of collagen, as can be seen in FIG. 15, which induces opacification of the lens capsule, thereby effecting an eventual loss of vision. But, through the usage of the fibrin annulus, in the manner as herein explained, it has been found that such migration of epithelial growth, with the eventual formation of fibroblasts, and collagen, is prevented.

As previously summarized, and as explained, it may be likely that the application of one of the biological or nonbiological glues, as previously explained, either in lieu of, or in addition, the application of fibrin, may likewise provide for the surface application of the IOL to the back wall or posterior of the capsule, and while inducing epithelial growth or creation of cells at the periphery of the lens, will prevent their migration centrally into the region behind the lens, and between it and the posterior wall of the capsule.

Variations or modifications to the subject matter of this invention may occur to those skilled in the art upon reviewing the disclosure herein. Such variations, if within the spirit of this invention, are intended to be encompassed within the scope of any claims to patent protection issuing upon this development. The description of the preferred embodiment set forth herein is done so for illustrative purposes only.

Having thus described the invention what is claimed and desired to be secured by Letters Patent is:

1. An intraocular lens (IOL) capable of implanting in the posterior chamber of a human eye and against its posterior wall after an extracapsular extraction, said IOL having an adhesive means applied to its backside thereof, such that said adhesive means creates a continuous peripheral barrier against the central migration of lens epithelium along the posterior capsule from which it attains support, and said IOL being adapted to be positioned within the chamber and to be sealed against said a posterior wall of the eye by means of said adhesive means.

2. The invention of claim 1 and including at least one haptic connecting with the lens for positioning said IOL in place within the lens capsule.

3. The intraocular lens of claim 1, wherein said adhesive means being applied to the outer periphery adjacent the backside of said IOL, said adhesive therein adapted to form continuous uninterrupted annulus between the implanted lens and the surface of the posterior wall.

4. The invention of claim 1 and wherein said adhesive means being applied over the entire backside of said IOL.

5. The intraocular lens of claim 1 and wherein said adhesive means being a glue which interacts with the patient's own tissue coagulation system for securely anchoring the IOL in place against the posterior capsule of the eye.

6. The invention of claim 5 and wherein said adhesive means comprising a biological glue.

7. The invention of claim 6 and wherein said biological glue comprises fibrin.

8. The invention of claim 6 and wherein said biological glue comprising a mussel glue.

9. The invention of claim 5 and wherein said adhesive means being a nonbiological glue.

10. The intraocular lens of claim 5, wherein said adhesive means comprising a fibrin based annular patch.

11. The invention of claim 6, and wherein said adhesive means comprising a collagen formed annular patch.

12. The invention of claim 10 and wherein said annular patch being impregnated with collagen particles.

13. The invention of claim 10 and wherein said annular patch being impregnated with lyophilized fibronectin.

14. The invention of claim 10 and including a covering material overlying said fibrin patch, and said covering material being removable just prior to implanting of the IOL within the posterior capsule.

15. The invention of claim 10 and wherein fibrous connective tissue is adapted to grow around said annular patch is permanently binding said intraocular lens to the adjacent posterior wall of the eye.

16. An intraocular lens for implanting in the posterior chamber of a human eye after an extracapsular extraction, said lens having a backside, said intraocular lens having a biological adhesive applied to its backside as a continuous peripheral barrier, said biological adhesive being capable of interacting with the patient's own coagulation system, such that the connective tissue formed between said posterior wall and the biological adhesive permanently anchoring the said lens to its adjacent posterior wall.

17. An intraocular lens for implanting in the posterior chamber of a human eye after an extracapsular extraction, wherein said intraocular lens having an adhesive applied thereto, a first adhesive applied to the outer circumference of the backside of the lens, and a different adhesive applied centrally to the backside thereof, and with said combined adhesives providing for adherence of the IOL to the posterior wall and thereby permanently anchoring of the said lens within the posterior capsule.

18. The invention of claim 2 and wherein said positioning haptic being dissolvable within the eye.

19. The invention of claim 18 and wherein said positioning haptic is absorbable.

20. The IOL of claim 6 and wherein said glue is applied to the backside of said IOL is in the form of an annulus.

21. The IOL of claim 6 wherein said glue is optically transparent when dry and is placed over the entire backside of the said lens during implanting.

22. The invention of claim 6 and including at least one haptic connecting with the lens for positioning said IOL in place within the lens capsule, said haptic being dissolvable within the eye, and said haptic being absorbed and dissolved after said glue has set and the usage of the haptics being no longer required.

23. An IOL, for implant within the human eye after extracapsular extraction, wherein said IOL is for positioning within the posterior capsule of the eye by means of a nontoxic, nonabsorbable, nonbiological glue, and wherein said glue being applied to at least a continuous peripheral portion of the back of the IOL just prior to its implanting.

24. The IOL of the claim 23 and wherein said glue is applied as an annulus around the outer back periphery of the IOL just prior to implanting.

25. The invention of claim 23 and wherein said glue being applied to the entire backside of the IOL prior to its implanting.

26. The IOL of claim 25 and including haptics, said haptics extending from the IOL, said haptics being dissolvable and absorbable within the eye after said glue has set.

27. The invention of claim 26 and wherein said glue creates a barrier to migration of ephithelium and thereby preventing opacification of the posterior chamber contiguous with the lens during IOL implant.

28. The invention of claim 23 and wherein said glue being a isocyanoacrylate glue.

29. An intraocular lens for implanting in the posterior chamber of a human eye after an extracapsular extraction, wherein said intraocular lens having an adhesive means applied thereto, said adhesive means being applied to the backside of the lens, said adhesive means being applied to the entire outer circumference of the backside of said lens, and with said adhesive providing for adherence of the intraocular lens to a posterior wall of any human eye and thereby permanently anchoring of the said lens within the eye's posterior capsule.

* * * * *